US008657844B2

(12) United States Patent
You et al.

(10) Patent No.: US 8,657,844 B2
(45) Date of Patent: Feb. 25, 2014

(54) MEDICAL EXPANDING APPARATUS

(75) Inventors: Chang-Hwa You, Gyeonggi-do (KR); Boo-Gou Park, Incheon (KR)

(73) Assignee: BM Korea Co., Ltd, Gunpo-si (KR)

( * ) Notice: Subject to any disclaimer, the term of this patent is extended or adjusted under 35 U.S.C. 154(b) by 0 days.

(21) Appl. No.: 13/055,929

(22) PCT Filed: May 14, 2010

(86) PCT No.: PCT/KR2010/003043
§ 371 (c)(1),
(2), (4) Date: Oct. 19, 2011

(87) PCT Pub. No.: WO2011/142491
PCT Pub. Date: Nov. 17, 2011

(65) Prior Publication Data
US 2012/0053610 A1    Mar. 1, 2012

(51) Int. Cl.
*A61M 29/00* (2006.01)
(52) U.S. Cl.
USPC .......................................................... 606/192
(58) Field of Classification Search
USPC ................ 600/184; 604/97.01, 97.02, 97.03, 604/98.01, 98.02, 284, 538; 606/190, 191, 606/192, 193, 194, 195, 198
See application file for complete search history.

(56) References Cited

U.S. PATENT DOCUMENTS

| 4,877,031 | A | * | 10/1989 | Conway et al. | 606/194 |
| 5,129,887 | A | * | 7/1992 | Euteneuer et al. | 606/194 |
| 2002/0042625 | A1 | * | 4/2002 | Stack et al. | 606/194 |

* cited by examiner

*Primary Examiner* — Ryan Severson
*Assistant Examiner* — Jonathan W Miles
(74) *Attorney, Agent, or Firm* — Intellectual Property Law Group LLP

(57) ABSTRACT

A medical expanding apparatus is disclosed that can separate adhered neural tissues or muscle tissues. The apparatus includes an expanding member, an air tube, a connecting part, a body, and a front cover. The expanding member is expanded in the human body using air pressure. The air tube, whose one end is coupled to the expanding member, holds the expanding member and guides the air into the inside of the expanding member. The connecting part, whose one end is fitted into the other end of the air tube to be tightly coupled to the air tube, guides the air into the air tube. The body has an air inflow pipe and transfers the air flowing in through the air inflow pipe to the connecting part in order to expand the expanding member. One end of the body is coupled to the other side end of the connecting part. The front cover, coupled to the one end of the body, closely couples the connecting part and the body, so that the body holds the connecting part. The apparatus allows the expanding member to be stably expanded and prevents the air tube from being torn or damaged.

7 Claims, 2 Drawing Sheets

MEDICAL EXPANDING APPARATUS

BACKGROUND OF THE INVENTION

1. Field of the Invention

The present invention relates to a medical expanding apparatus that can separate adhered neural tissues or muscle tissues, using elastic and expandable thermoplastic-polyurethane, or can secure a space to insert solution treatment material into body tissues.

2. Description of the Related Art

In general, the human body contains fine blood vessels and tissue, etc., which may easily be damaged by a relatively small impact. The blood vessels and tissue may also be clogged by foreign matter, which can result in the loss of life. In that case, the foreign matter must be removed from the clogged organ in a short time. If the fine blood vessels or tissues are adhered due to an inflammation or cancer, their functions become weak. In that case, medicinal substances cannot be medicated to the precise position where the corresponding disease has occurred. Therefore, the patient receives an excessive amount of an antibiotic drug or an anticancer drug.

In a dental area, when the alveolar bone fusion is performed, an alveolar bone in the teeth ridge of the upper jaw becomes necrotic, so conglutination frequently occurs between nerves or between nerves and tissue. In conventional technology, the alveolar bone fusion is performed by a metal device or equipment using high heat. In that case, the conglutinated nerves in the upper jaw are damaged, which can cause facial paralysis or even death.

In an emergency situation, the trachea of an injured person may be clogged by foreign matter. In that case, the injured person has difficulty breathing and may lose his/her life. In conventional technology, when an injured person requires first-aid treatment, trachea expansion has been performed using a metal device. However, the conventional metal device may damage the esophagus. It has a limitation to exert its function according to the type of foreign matter or the clogging depth.

In renal medicine, when a urethral canal expansion is performed, a calculus comes down to the bladder and then enters the urethra during the urination. In that case, the patient is in such serious pain such that he/she cannot walk. In conventional technology, the calculus is removed by incising the urethra or pulverized it by shock waves generated by external equipment. However, this conventional technology is disadvantageous in that it leaves a scar or damages the urethral tissue. It has also a high recurrence rate.

In order to resolve these problems, various types of devices having an expandable structure have been proposed. For example, a conventional device having an expandable structure is configured to be associated with an actuator or a manipulator for generating air pressure, so that it adjusts the volume or pressure of its expandable structure, according to the size of a blood vessel or a conglutinating force of neural tissues or muscle tissues, using air pressure generated by the actuator or a manipulator. Based on the operation principle described above, the conventional device having an expandable structure removes the conglutinated neural tissues or muscle tissues and expands the organ clogged by foreign matter, thereby easily removing the foreign matter. During this operation, contrast media is mixed with disinfected distilled water and then the mixture is used in the actuator or the manipulator for generating pressure in order to check the position and the volume of the expandable structure. After resolving the conventional problems, medical substances in solution, such as anticancer drug or antibiotic drug, are medicated to the damaged tissues.

FIG. 1 is a cross-sectional view illustrating a conventional medical expanding apparatus. Referring to FIG. 1, the medical expanding apparatus includes a body 15, an air tube 12 connected to the body 15, an auxiliary tube 13 contained in the air tube 12, and a long needle 18 contained in the auxiliary tube 13. The body 15 is coupled with a rear cap 17 connected to the long needle 18. The body 15 has an air inflow tube 16 to which an air pipe 21 and an external air injecting device (not shown) are connected.

The conventional medical expanding apparatus has the following problems.

Since the air tube 12 is not tightly connected, at the portion 10, to the body 15, they may become separated at the portion 10, so that an expandable structure (not shown) loses its expansion function. The long needle 18 made of metal is fixed to the rear cap 17. The rear cap 17 is detachably screw-coupled to the body 15. If the rear cap 17 is not fully coupled to the body 15, the long needle 18 is not aligned with the air tube 12, which causes the air tube 12 to be torn or damaged.

SUMMARY OF THE INVENTION

The present invention solves the above problems, and provides a medical expanding apparatus that can stably perform an expansion.

In accordance with an exemplary embodiment of the present invention, there is provided a medical expanding apparatus including: an expanding member for being expanding in the human body using air pressure; an air tube, whose one end is coupled to the expanding member, for holding the expanding member and for guiding the air into the inside of the expanding member; a connecting part, whose one end is fitted into the other end of the air tube to be tightly coupled to the air tube, for guiding the air into the air tube; a body having an air inflow pipe, for transferring the air flowing in through the air inflow pipe to the connecting part in order to expand the expanding member, wherein one end of the body is coupled to the other end of the connecting part; and a front cover, coupled to the one end of the body, for closely coupling the connecting part and the body, so that the body holds the connecting part.

Preferably, the connecting part and the air tube is welded.

Preferably, the connecting part is formed with a tapered inner portion through which air passes, so that the expanding member can be expanded by the air at the same pressure as the air flowing in the body.

Preferably, the medical expanding apparatus may further include an O-ring between the body and the connecting part, for preventing air leakage.

Preferably, the body includes grips.

Preferably, the air inflow pipe forms a thread to which an injector for injecting air to the body can be directly coupled.

Preferably, the medical expanding apparatus may further include: an auxiliary tube for holding the expanding member and the air tube, the auxiliary tube extending through the body, the connecting part, and the air tube to the expanding member; a rear cover coupled to the other end of the body; and a long needle fixed to the rear cover, for holding the auxiliary tube, the long needle extending through the auxiliary tube to the expanding member. The rear cover is welded to the body, so that the long needle does not damage the air tube.

Preferably, the auxiliary tube comprises a platinum ring at its one end toward the expanding member.

BRIEF DESCRIPTION OF THE DRAWINGS

The features and advantages of the present invention will become more apparent from the following detailed description in conjunction with the accompanying drawings, in which.

BRIEF DESCRIPTION OF SYMBOLS IN THE DRAWINGS

Figure 1:
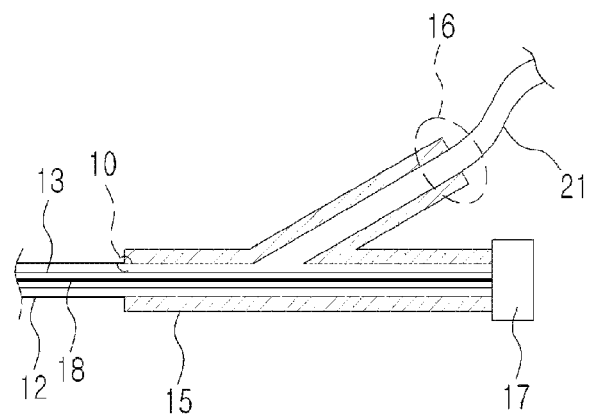
FIG. 1 is a cross-sectional view illustrating a conventional medical expanding apparatus.

100: medical expanding apparatus
110: expanding member
120: air tube
130: auxiliary tube
140: connecting part
145: O-ring
150: body
160: front cover
170: rear cover
180: long needle

DETAILED DESCRIPTION OF SPECIFIC EMBODIMENTS

Hereinafter, exemplary embodiments of the present invention are described in detail with reference to the accompanying drawings.

Figure 2:
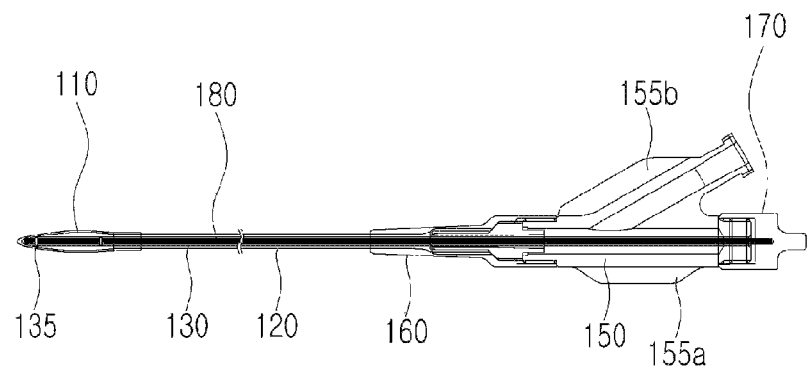
FIG. 2 is a cross-sectional view illustrating a medical expanding apparatus according to an embodiment of the present invention.
Figure 3:
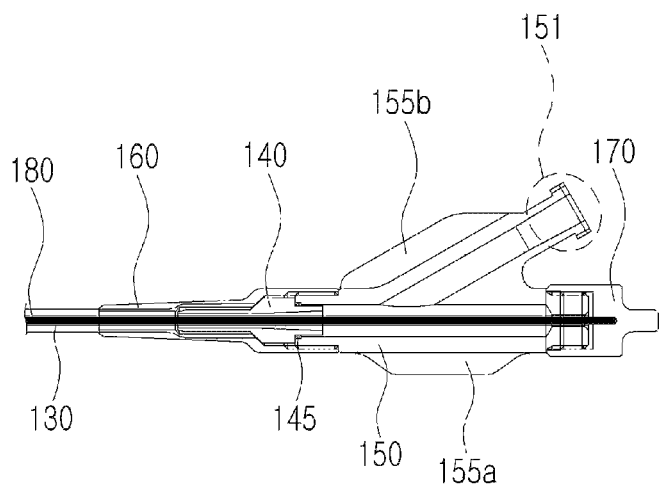
FIG. 3 is a cross-sectional view illustrating a part of the medical expanding apparatus according to an embodiment of the present invention.
Figure 4:
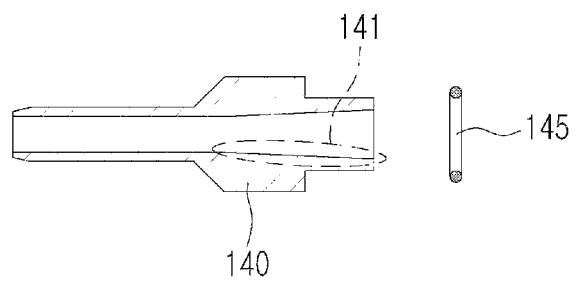
FIG. 4 is a cross-sectional view illustrating a connection part of the medical expanding apparatus according to an embodiment of the present invention.

FIG. 2 is a cross-sectional view illustrating a medical expanding apparatus according to an embodiment of the present invention. FIG. 3 is a cross-sectional view illustrating a part of the medical expanding apparatus according to an embodiment of the present invention. FIG. 4 is a cross-sectional view illustrating a connect ion part of the medical expanding apparatus according to an embodiment of the present invention.

Referring to FIGS. 2 to 4, the medical expanding apparatus 100 includes an expanding member 110, an air tube 120, an auxiliary tube 130, a connecting part 140, a body 150, a front cover 160, and a rear cover 170.

The body 150 receives air from an external air pressure generation system, such as an injector, and transfers it to the connecting part 140. The body 150 has an air inflow pipe 151 that receives air to expand the expanding member 110. One end of the body 150 is coupled to the other end of the connecting part 140.

When air, from the external air pressure generation system, flows in to the body 150 via the air inflow pipe 151, it passes through the connecting part 140 and the air tube 120 and then flows in to the expanding member 110, thereby expanding the expanding member 110.

It is preferable that the air inflow pipe 151 forms a thread (not shown) to be coupled to an injector (not shown). If an injector is directly connected to the air inflow pipe 151, the air from the injector can more rapidly expand the expanding member 110. In that case, an air pipe is not required between the body 150 and the injector. That is, the injector is directly connected to the body via the air inflow pipe. The tapered inner shape of the connecting part 140 minimizes the lowering of air pressure but instead provides sufficient air pressure to the expanding member 110.

It is preferable that the body 150 has grips 155a and 155b that a user can hold.

The connecting part 140 guides air from the outside to the air tube 120, so that the air can flow into the body 150. The connecting part 140 is tightly coupled to the air tube 120. That is, the one end of the connecting part 140 is tightly fitted into the other end of the air tube 120.

It is preferable that the one end of the connecting part 140 is tapered toward the end, so that it can be easily fitted into the other end of the air tube 120. Since the one end of the connecting part 140 is located inside the other end of the air tube 120, the connecting part 140 and the air tube 120 can be tightly coupled to each other. In particular, if the coupling between the connecting part 140 and the air tube 120, described above, is sealed by a welding method, for example, air leakage can be more effectively prevented.

In an embodiment of the present invention, the coupling between the connecting part 140 and the air tube 120 is sealed by a welding method, to prevent air from leaking. It is preferable that the connecting part 140, the air tube 120, and the expanding member 110 are all welded.

In the connecting part 140, its inside 141 through which air flows is tapered, so that the expanding member 110 can be expanded by the air at the same pressure as the air flowing into the body 150. The tapered inside 141 of the connecting part 140 can allow the air, whose pressure is lowered in the body 150, to raise its pressure again and then to flow it into the expanding member 110 via the air tube 120.

It is preferable that an O-ring 145 is placed between the connecting part 140 and the body to prevent air leakage. When the front cover 160 is coupled to the body 150, it pushes the connecting part 140 to the body 150, so that the O-ring 145 closely seals the gap between the connecting part 140 and the body 150, which prevents the air leakage.

Contrast media (not shown) mixed with disinfected distilled water must be rapidly transferred to the expanding member 110, so that the user can check the volume or state of the expanding member 110 that is being expanded. The connecting part 140, directly fixed to the air tube 120, increases the air pressure, lowered in the body 150, via its tapered inside 141, thereby rapidly transferring the contrast media to the expanding member 110. In contrast, the tapered inside 141 also serves to minimize the air pressure returned from the expanding member 110.

The front cover 160 is coupled to one end of the body, so that the connecting part 140 can be tightly coupled to the body 150. The front cover 160 holds the connecting part 140. It is preferable that the front cover 160 has a tapered portion contacting the connecting part 140, as shown in FIG. 3, so that it can effectively couple the connecting part 140 and the body 150.

The front cover 160 may also serve to protect a coupling portion between the air tube 120 and the connecting part 140.

The air tube 120 guides air that flows in via the connecting part 140 to the inside of the expanding member 110, so that the air can expand the expanding member 110 with a certain pressure. The air tube 120 holds the expanding member 110. One end of the air tube 120 is welded with the expanding member 110 to prevent leakage.

The air tube 120 contains an auxiliary tube 130. The other end of the air tube 120 is coupled to the connecting part 140. It is preferable that the coupling between the other end of the air tube 120 and the connecting part 140 is welded to prevent air leakage. The connecting part 140 holds the air tube 120.

The expanding member 110 is expanded, by air flowing in via the air tube 120, in the human body. That is, the expanding member 110 is inserted into the human body, for example, neural tissues, muscle tissues, etc., and then expanded, thereby separating adhered neural tissues or muscle tissue and neural tissue, or securing a space to insert solution treatment material into the body tissues.

The expanding member 110 is coupled to one end of the air tube 120, so that it can be expanded by air flowing therein via the air tube 120.

It is preferable that the expanding member 110 is made of a material with good elasticity and expansion, for example, thermoplastic polyurethane.

The auxiliary tube 130 serves to hold the expanding member 110 and the air tube 120. The auxiliary tube 130 passes through the body 150, the connecting part 140, and the air tube 120 and reaches the expanding member 110. The auxiliary tube 130 contains a long needle 180. The one end of the long needle 180 is fixed to the rear cover 170, and holds and guides the auxiliary tube 130 so that the user can locate the expanding member 110 at a certain position.

Air flowing in from the outside flows in via the space between the auxiliary tube 130 and the air tube 120 to the expanding member 110, thereby expanding the expanding member 110.

A platinum ring 135 serves as a marker to indicate the position of the expanding member 110.

The platinum ring 135 is mounted at the one end of the auxiliary tube 130 and placed inside the expanding member 110. In an embodiment of the present invention, as shown in FIG. 2, two platinum rings 135 are mounted to the one end of the auxiliary tube 130.

For example, if radioactive rays are applied to a corresponding portion of the human body using radiation equipment, such as C-ARM, the platinum ring 135 receives the radioactive rays and reflects them. The rays reflected from the platinum ring 135 show the position of the expanding member 110.

The long needle 180, fixed to the rear cover 170, holds and guides the auxiliary tube 130. The rear cover 170 holds the long needle 180.

The rear cover 170 is coupled to the other end of the body 150, preferably in a welding manner. The long needle 180, fixed to the rear cover 170, extends through the auxiliary tube 130 to the expanding member 110, and holds the auxiliary tube 130. The auxiliary tube 130, supported by the long needle 180, holds the air tube 120 and the expanding member 110. It is preferable that the long needle 180 is made of an elastic metal material.

Since the rear cover 170, to which the long needle 180 is fixed, is welded to the body, the long needle 180 can be aligned with the air tube 120, thereby preventing the damage of air tube 120 from the long needle 180.

As described above, since the medical expanding apparatus according to the present invention is configured in such a way that the connecting part, whose inside is tapered, is fixed to the air tube and the front cover tightly couples the connecting part to the body, the air tube can stably receive air from the body and flows it out to the expanding member, so that the expanding member can exert its expansion function.

Since the rear cover to which the long needle is fixed is fixedly coupled to the body, the medical expanding apparatus can prevent the air tube from being torn or damaged by the long needle, thereby enhancing its operation reliability and stability.

Since the injector can be directly coupled to the air inflow pipe of the body, the medical expanding apparatus can rapidly expand the expanding member in an emergency situation.

Although exemplary embodiments of the present invention have been described in detail hereinabove, it should be understood that many variations and modifications of the basic inventive concept herein described, which may appear to those skilled in the art, will still fall within the spirit and scope of the exemplary embodiments of the present invention as defined in the appended claims.

What is claimed is:

1. A medical expanding apparatus comprising:
   an expanding member for being expanded in the human body using air pressure;
   an air tube, whose one end is coupled to the expanding member, for holding the expanding member and for guiding the air into the inside of the expanding member;
   a connecting part, whose one end is fitted into the other end of the air tube to be tightly coupled to the air tube, for guiding the air into the air tube;
   a body having an air inflow pipe, for transferring the air flowing in through the air inflow pipe to the connecting part in order to expand the expanding member, wherein one end of the body is coupled to the other end of the connecting part; and
   a front cover, coupled to the one end of the body, for closely coupling the connecting part and the body, so that the body holds the connecting part;
   wherein the connecting part is formed with a tapered inner portion through which air passes, so that the expanding member can be expanded by the air at the same pressure as the air flowing in the body.

2. The medical expanding apparatus according to claim 1, wherein the connecting part and the air tube is welded.

3. The medical expanding apparatus according to claim 1, further comprising an O-ring between the body and the connecting part, for preventing air leakage.

4. The medical expanding apparatus according to claim 1, wherein the body comprises grips.

5. The medical expanding apparatus according to claim 1, wherein the air inflow pipe forms a thread to which an injector for injecting air to the body can be directly coupled.

6. The medical expanding apparatus according to claim 1, further comprising:
   an auxiliary tube for holding the expanding member and the air tube, the auxiliary tube extending through the body, the connecting part, and the air tube to the expanding member;
   a rear cover coupled to the other end of the body; and
   a long needle fixed to the rear cover, for holding the auxiliary tube, the long needle extending through the auxiliary tube to the expanding member,
   wherein the rear cover is welded to the body, so that the long needle does not damage the air tube.

7. The medical expanding apparatus according to claim 6, wherein the auxiliary tube comprises a platinum ring at its one end toward the expanding member.

* * * * *